US008864665B2

(12) United States Patent
Rotondo et al.

(10) Patent No.: US 8,864,665 B2
(45) Date of Patent: Oct. 21, 2014

(54) METHOD AND DEVICE FOR MONITORING THE RISKS FOR SUDDEN INFANT DEATH SYNDROME AND FOR POSITIONAL PLAGIOCEPHALY

(75) Inventors: Giuseppe Rotondo, Milan (IT); Iuri Frosio, Sorisole (IT)

(73) Assignee: Alta Lab S.r.l. (IT)

( * ) Notice: Subject to any disclaimer, the term of this patent is extended or adjusted under 35 U.S.C. 154(b) by 214 days.

(21) Appl. No.: 13/227,154

(22) Filed: Sep. 7, 2011

(65) Prior Publication Data

US 2012/0083670 A1 Apr. 5, 2012

(30) Foreign Application Priority Data

Sep. 7, 2010 (IT) .................................. MI10A1613
Jul. 7, 2011 (EP) ..................................... 11173092

(51) Int. Cl.
*A61B 5/00* (2006.01)
*A61B 5/113* (2006.01)
*A61B 5/11* (2006.01)
*A61B 5/08* (2006.01)

(52) U.S. Cl.
CPC ............... *A61B 5/1116* (2013.01); *A61B 5/113* (2013.01); *A61B 5/4818* (2013.01); *A61B 2503/04* (2013.01); *A61B 5/4806* (2013.01); *A61B 2560/0412* (2013.01); *A61B 5/7275* (2013.01); *A61B 2562/0219* (2013.01); *A61B 5/6814* (2013.01); *A61B 5/6823* (2013.01); *A61B 5/0816* (2013.01); *A61B 5/6804* (2013.01)
USPC ......................................................... 600/301

(58) Field of Classification Search
CPC ..................... A61B 2503/04; A61B 2503/045; A61B 5/00
USPC ..................... 600/300–301; 340/573.1; 5/655
See application file for complete search history.

(56) References Cited

U.S. PATENT DOCUMENTS 4,440,177 A 4/1984 Anderson et al.
4,738,266 A 4/1988 Thatcher
(Continued)

FOREIGN PATENT DOCUMENTS

CA 2207322 A1 6/1996
JP 2008048819 A 3/2008
(Continued)

OTHER PUBLICATIONS

Snapshot of "www.angelcare--monitor.com/United-States/en/products"; of Apr. 12, 2010 available at archive.org; 2 pages.
(Continued)

*Primary Examiner* — William Thomson
*Assistant Examiner* — Bobby Soriano
(74) *Attorney, Agent, or Firm* — St. Onge Steward Johnston & Reens LLC

(57) ABSTRACT

A portable monitoring device for monitoring of the short term, mid term and long term risks of Sudden Infant Death Syndrome (SIDS) and to estimate the risk of onset of positional plagiocephaly. The monitoring device acquires one or more signals associated to the typical breath and positioning patterns of an infant through a tri-axial accelerometer, and registers the data in electronic format, where statistical analysis of the signal and pattern recognition are performed in real time by a processing unit. The device monitors the breath activity of an infant in various conditions, alerting a caregiver when a potentially dangerous situation is detected. The monitoring is attached to the clothes of the infant. Statistical analysis of the registered data is performed for quantifying the long term SIDS risk, the risk of plagiocephaly and for optimizing the functional parameters of the monitoring device.

19 Claims, 4 Drawing Sheets

(56) References Cited

U.S. PATENT DOCUMENTS

| | | | |
|---|---|---|---|
| 5,241,300 | A | 8/1993 | Buschmann |
| 5,505,199 | A | 4/1996 | Kim |
| 5,515,865 | A | 5/1996 | Scanlon |
| 5,864,291 | A | 1/1999 | Walton |
| 5,914,660 | A | 6/1999 | Mesibov et al. |
| 6,011,477 | A * | 1/2000 | Teodorescu et al. ....... 340/573.1 |
| 6,047,201 | A | 4/2000 | Jackson, III |
| 6,150,941 | A | 11/2000 | Geiger et al. |
| 6,373,392 | B1 | 4/2002 | Au |
| 6,468,234 | B1 * | 10/2002 | Van der Loos et al. ....... 600/595 |
| 6,765,489 | B1 | 7/2004 | Ketelhohn |
| 6,975,230 | B1 * | 12/2005 | Brilman ...................... 340/573.1 |
| 7,153,284 | B2 | 12/2006 | Argenta |
| 7,567,200 | B1 * | 7/2009 | Osterweil ........................ 342/28 |
| 7,698,763 | B2 | 4/2010 | Warnock |
| 7,733,224 | B2 * | 6/2010 | Tran .............................. 340/540 |
| 7,961,093 | B2 * | 6/2011 | Chiao et al. .............. 340/539.26 |
| 8,094,013 | B1 * | 1/2012 | Lee et al. .................. 340/539.15 |
| 8,502,679 | B2 * | 8/2013 | Ayon et al. ................. 340/573.1 |
| 2002/0133067 | A1 | 9/2002 | Jackson, III |
| 2006/0020221 | A1 | 1/2006 | Silpachai et al. |
| 2006/0047217 | A1 | 3/2006 | Mirtalebi et al. |
| 2006/0097879 | A1 | 5/2006 | Lippincott |
| 2007/0244404 | A1 | 10/2007 | Haghighi-Mood et al. |
| 2008/0015457 | A1 | 1/2008 | Silva |
| 2008/0094226 | A1 * | 4/2008 | O'Shea et al. ............. 340/573.1 |
| 2008/0262381 | A1 | 10/2008 | Kolen |
| 2009/0151080 | A1 * | 6/2009 | Lord ................................. 5/655 |
| 2010/0079292 | A1 * | 4/2010 | Lynn et al. ................. 340/573.1 |
| 2010/0081895 | A1 | 4/2010 | Zand |
| 2010/0217158 | A1 | 8/2010 | Wolfe et al. |
| 2010/0242180 | A1 * | 9/2010 | Warnock ........................... 5/637 |
| 2013/0043999 | A1 * | 2/2013 | Van Beest ................. 340/573.7 |

FOREIGN PATENT DOCUMENTS

| | | | |
|---|---|---|---|
| WO | 9618176 | A1 | 6/1996 |
| WO | 0108556 | A1 | 2/2001 |
| WO | 2008026812 | A1 | 3/2008 |
| WO | 2008079296 | A1 | 7/2008 |

OTHER PUBLICATIONS

User Manual Angelcare AC 100 of Aug. 9, 2002; 33 pages.
User Manual Angelcare AC 301 and AC 301-R of Jul. 14, 2006; 13 pages.
Uchiyama, T., et al.; "Color Image Segmentation Using Competitive Learning"; IEEE Transactions on Pattern Analysis and Machine Intelligence, vol. 16, No. 12, Dec. 1994; p. 1197-1206.
Gonzalez, R. C., Woods, E.: Digital Image Processing; Prentice Hall International; 2008; pp. 1-195.
Gonzalez, R. C., Woods, E.: Digital Image Processing; Prentice Hall International; 2008; pp. 196-401.
Gonzalez, R. C., Woods, E.: Digital Image Processing; Prentice Hall International; 2008; pp. 402-609.
Hathaway, R J., et al:; "Generalized Fuzzy c-Means Clustering Strategies Using Lp Norm Distances"; IEEE Transactions on Fuzzy Systems; vol. 8, No. 5, Oct. 2000; p. 576-582.
Bishop, C. M.; "Pattern Recognition and Machine Learning"; Information Science and Statistics; 2006; pp. 1-749.
Caccamese J, Costello BJ, Ruiz RL, Ritter AM (2004). "Positional plagiocephaly: evaluation and management". Oral Maxillofac Surg Clin North Am 16 (4): 439-46.
John Persing, Hector James, Jack Swanson, John Kattwinkel: "Prevention and Management of Positional Skull Deformities in Infants", Pediatrics 2003;112;199-202.
SIDS Rate Source: CDC, National Center for Health Statistics; SIDS Rate and Back Sleeping (1988-2006); http://www.nichd.nih.gov/SIDS/upload/SIDS_rate_back_sleep_2006.pdf 2006; 1 page.
Turk AE, McCarthy JG, Thorne CH, Wisoff JH (1996). "The "back to sleep campaign" and deformational plagiocephaly: is there cause for concern?". J Craniofac Surg 7 (1): 12-8.
Angelcare® AC401—Rechargeable Movement & Sound Monitor; www.angelcare-monitor.com; May 20, 2011; 18 pages.
European Search Report Application No. EP 11 17 3092 Completed: Nov. 17, 2011; Mailing Date: Mar. 19, 2012 11 pages.
Van Laerhoven, K, et al.; Sustained logging and discrimination of sleep postures with low-level, wrist-worn sensors; 12th IEEE International Symposium on Wearable Computers, 2008; Sep. 28, 2008; p. 69-76.

* cited by examiner (a)

(b)

METHOD AND DEVICE FOR MONITORING THE RISKS FOR SUDDEN INFANT DEATH SYNDROME AND FOR POSITIONAL PLAGIOCEPHALY

CROSS-REFERENCE TO RELATED APPLICATIONS

This present application claims priority of Italian patent application No. MI2010A001613 filed on Sep. 7, 2010, and of European patent application No. 11 173 092.5 filed on Jul. 7, 2011, the disclosures of both of which are hereby incorporated by reference in its entirety as part of the present disclosure.

FIELD OF THE INVENTION

The invention relates to a method and a portable monitoring device for monitoring the short term, mid term and long term risks of Sudden Infant Death Syndrome (SIDS) and the risk of onset of positional plagiocephaly.

The invention further relates to a software program product assessing long term risks.

BACKGROUND OF THE INVENTION

It is nowadays well known that sleeping in a supine position significantly reduces the risk of SIDS [25], [26], [27]. Since the "back to sleep campaign" launched in 1992 by the American Academy of Pediatrics, all pediatricians suggest to the parent to place their children on their back when they sleep in the first year of life; as a consequence, the occurrence of SIDS has been greatly reduced (from 1.4 per 1,000 live births in 1988 to 0.55 per 1,000 live births in 2003). However, the causes of SIDS mainly remain undiscovered, and its incidence is even nowadays beyond 0.5 per 1000 births. Moreover, probably because of the predominant supine sleeping position, the occurrence of positional plagiocephaly has tremendously increased since 1992. This is probably associated to the fact that, because of a repetitive pressure applied to the soft infant head bone, for instance during the sleep, the infant skull changes its shape [24], [25]. In this case, some helmets are sometimes applied to correct the shape of the skull, but their efficacy is questioned [28], [29]. A more common solution suggested by the pediatricians is to adopt a strategy of "repositioning", in other words try to make sleep the children on a side (the opposite with respect to the compressed skull area) as long as possible.

Some special pillows [30] can be used to this scope, but it is clear that a continuous supervision cannot be performed; in this sense, the analysis of the infant orientation during the night can represent a significant instrument, both to prevent the outcome of plagiocephaly and to control the efficacy of the infant repositioning strategy.

Different systems have been proposed for monitoring the breath of an infant, with the aim of preventing the occurrence of SIDS.

The most reliable of them adopts costly technologies, which can be used only by skilled people in a clinical scenario. For instance, in [1, 2] some devices which analyze the levels of O2 and CO2 in the infant breath are disclosed; in [3, 4], a pulse oxymeter is mounted onto the feet of the infant for measuring the blood oxygen and heart pulse rate; other systems are based on electrodes [5], air mattresses equipped with pressure sensors [6], measurements of the room and expired breathe humidity [7]; video systems [8, 9] or constellation of different kinds of sensors [10, 11] have also been exploited: these permit the infant orientation to be estimated, which is an important factor in evaluating the risk of SIDS, as it has been demonstrated that infants sleeping in a supine position have a lower risk of SIDS with respect to infants sleeping in prone position. However, it should be clear that, because of their complexity and cost, these systems cannot be adopted in the normal home scenario by untrained people.

More easy-to-use systems have been proposed to this scope. Most of them are based on a sensorized pad [12], which has to be positioned under the mattress; because of its simplicity and low cost, this kind of systems is widely diffused, at least in Italy (see Angelcare® by Foppapedretti [13]). However, this approach suffers some significant drawbacks: the system is not easily transportable, as is has to be removed from under the mattress and repositioned if necessary; moreover, in the case when the infant moves during the sleep (very frequently occurring after the sixth month of life), he can shift with respect to the sensor area; in this case, the system cannot detect the infant movements and a false alarm is generated.

This can contribute to generate a status of anxiety in the caregivers that suddenly weak up in the night, and bring them after a significant number of false alarms to a lack of confidence in the monitoring system and consequently to abandon it.

Wearable/contact sensors represent a more reliable choice with respect to the problem of the false alarms. In [14], pressure and temperature transducers are used to estimate the infant attitude and to detect possible SIDS events; a transmitter/receiver pair is used to alert the caregiver of any risk situation. In [15] a marker based (and costly) video system is coupled with gravity sensors to estimate in real time the infant position; a signal is emitted when the infant is in a dangerous situation (for instance, prone sleeping) to force him to move in a different position. In [16] a device for monitoring the infant breath activity through a microphone is disclosed; however, ambient noise could represent a problem for this kind of system, leading to a potentially undetected SIDS event. In [17, 18, 19], a detector including a piezoelectric element is attached with a strap to the chest of the infant to detect its breath, and communicates an alarm to a receiver device in case of null detection; however, such system could be uncomfortable for the infant, or impractical for the parents each time the infant clothes have to be changed. A similar system, based on a trans-illuminated optical fiber, is described in [20].

Accelerometers can be used to construct wearable devices for breath monitoring. In [21], a pendant acceleration sensor, attached to the infant, communicates via wireless with a monitor device; in absence of movements (possible SIDS event), an alarm can be generated. In [22], an accelerometer-based system for controlling both animals and infants is described.

The inventors of [23] disclose an accelerometer-based system for detecting the lack of motion of an infant; the system is also capable to distinguish between different kinds of movements; when a lack of motion is detected, it stimulates the infant through a buzzer, with the aim of resuscitating him. The system is attached to the infant clothing, but no securing means is provided for avoid ingestion, which could represent a significant aspect for any wearable system composed by small pieces. A band pass filter, not including the DC component, is used to isolate the typical frequencies associated to breathing and movements. This can be a problem if one wants to estimate the infant orientation, which is in facts associated with the zero frequency component of the spectrum. Moreover, the housing of the sensor is rigid: this could be an uncomfortable situation for the infant. Lastly, a transmitter/receiver system is necessary to get the data from the sensor module.

Another accelerometer-based system for controlling the orientation and breathing of a sleeping infant is disclosed in [24]. Wireless technology is in this case necessary to guarantee that the sensor module can communicate the data to a different base module, which executes the data processing, and to the caregiver. In particular, it is highlighted that different communication channels (from Internet to the mobile phone net) can be used to alert the caregiver. Short data registration sequences, performed in a controlled environment (that is, when the caregiver can assure that the infant is sleeping and breathing), can be used in this case to optimize the sensor sensitivity (learning mode). Fast/Short Fourier Transforms, Auto Regressive models and Root Mean Squared are used to detect that the infant is breathing.

A skin temperature sensor is also included to assure that the sensor module is effectively attached to the infant body.

It appears evident from what above described that the prior art has in most part aimed to simply controlling in real time the breath (and sometimes also the orientation) position of an infant, to alert a caregiver when a potentially dangerous situation occurs related to a SIDS event.

It also appears evident that the prior art has proposed systems that can only be used in a controlled environment, such as a hospital bed or the bed in which the infant usually sleeps. Moreover, the existing commercial systems are usually composed by a set of at least two pieces (e.g. a sensor module and a data processing/alarm module), that are both necessary to guarantee the proper functioning of the system.

The prior art has anyway failed to propose an easily portable system, composed by a single piece, which can be comfortably worn by the infant with the assistance by the caregiver. Moreover, none of the cited prior art gives the possibility to record the breathing/positioning data for further processing. In this sense, none of them can provide useful indications about the long term SIDS risk, the possible outcome of plagiocephaly, or about the efficacy of the repositioning strategy.

SUMMARY OF THE INVENTION

Proceeding from this related art, the present invention seeks to provide an improved method, monitoring device and software program product for monitoring SIDS and positional plagiocephaly.

This object is achieved by a method, a monitoring device and a software program product having the features of the independent claims. Advantageous embodiments and refinements are specified in claims dependent thereon.

The wearable monitoring device is capable to acquire one or more signals associated to the typical breath and positioning patterns of an infant through a sensor device, for instance a tri-axial accelerometer, and to register the data in electronic format within the wearable monitoring device. Generally, the signal data are exclusively stored in the memory of the monitoring device.

The internal control circuits of the monitoring device perform a real time processing of the signals based on statistical analysis and pattern recognition. This allows an alarm to be generated in presence of a high, short or mid term SIDS risk, or in presence of risk of positional plagiocephaly.

When a sufficient amount of data is available, data can be downloaded on a standard PC; in this case, statistical analysis of the acquired data allows a personalized, long term SIDS risk factor to be estimated for each infant. The statistical analysis of the recorded data also allows identification of the eventually preferential sleeping position of the infant (e.g. on the right side), which can be associated to frequent compression of a side of the skull and consequent onset of plagiocephaly.

The analysis of the recorded data can finally be utilized to optimize the functional parameters of the monitoring device.

Data transferring occurs through a standard USB port of the monitoring device, which can also be used for recharging a battery of the monitoring device.

The system can be used for monitoring the breath activity of an infant in various conditions, alerting a caregiver when a potentially dangerous situation is detected.

Thanks to its simplicity of use, small encumbrance and low power consumption, the monitoring device can be turned on and attached to the clothes of the infant for as long as one day (or more), without the need of further supervision.

Registered data can therefore be utilized for quantifying the long term SIDS risk, the risk of plagiocephaly and for optimizing the functioning of the same monitoring device.

BRIEF DESCRIPTION OF THE DRAWINGS

The features and advantages of the present invention will result evident from the following detailed description of a preferred embodiment, illustrated as a non limiting example by the annexed figures, in which.

DETAILED DESCRIPTION OF THE INVENTION

Figure 1:
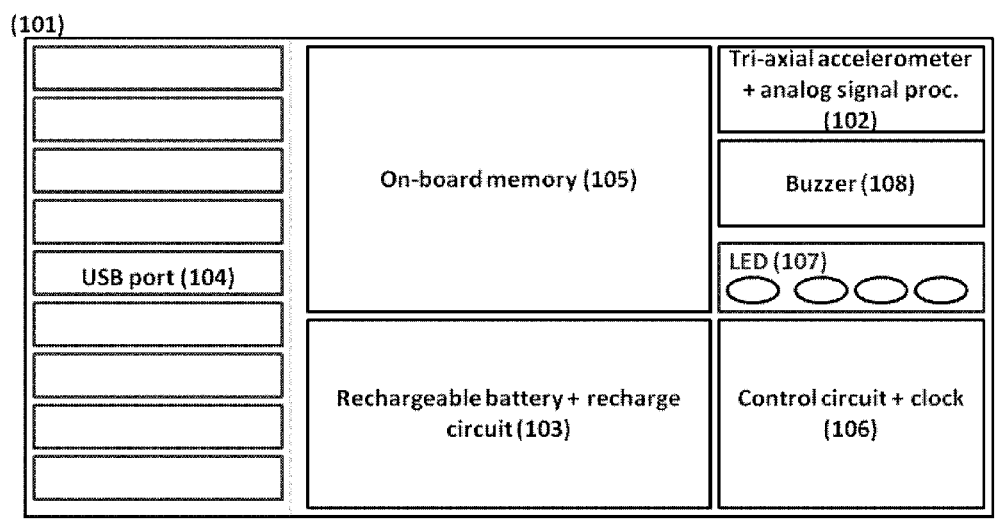
FIG. 1 illustrates an embodiment of the monitoring device used for measuring the infant breath and orientation, storing the data and emitting a signal of alarm through a buzzer.
Figure 1:

FIG. 1 shows a monitoring device 101 for monitoring the risks of SIDS and positional plagiocephaly. The monitoring device 101 includes a block 102 composed by a triaxial accelerometer and by the analog circuits that are necessary to filter out the undesired frequencies, to avoid aliasing and other interference. All the modules of the monitoring device 101 are powered by the rechargeable battery 103, which is also connected to the USB port 104.

The monitoring device 101 also includes an on board memory 105, a control circuit or processing unit 106, four indicator LEDs 107 and a buzzer 108.

For easy transportation and use outside of the home environment of the proposed device, the rechargeable battery 103 (including the circuit for controlling the recharge process) is incorporated into the monitoring device 101 and it is connected to the USB port 104, such that current can flow from the USB port to the battery during the recharge process.

The battery 103 is connected to the other components of the monitoring device 101 and provides power to them. One of the colored LEDs 107 (for instance the red one) is activated when the battery level is low, to alert the caregiver that recharging is necessary; alternatively, an alarm sound could be emitted by the buzzer 108 to signal the need of recharge.

In the preferred embodiment, a tri-axial accelerometer 102 is present in the monitoring device 101; this is capable of measuring the gravity force, the local accelerations induced by the movements of an infant, and in particular the movements of the stomach induced by the breathing process. From the measured acceleration vector, the orientation of the sensor module (and, consequently, of the infant) can be estimated. The three analog output channels are low-pass filtered by the analog circuits to eliminate the undesired frequency components (e.g. above 35 Hz) and avoid aliasing or other interferences (for instance, the 50 Hz/60 Hz of the power net).

Figure 2:
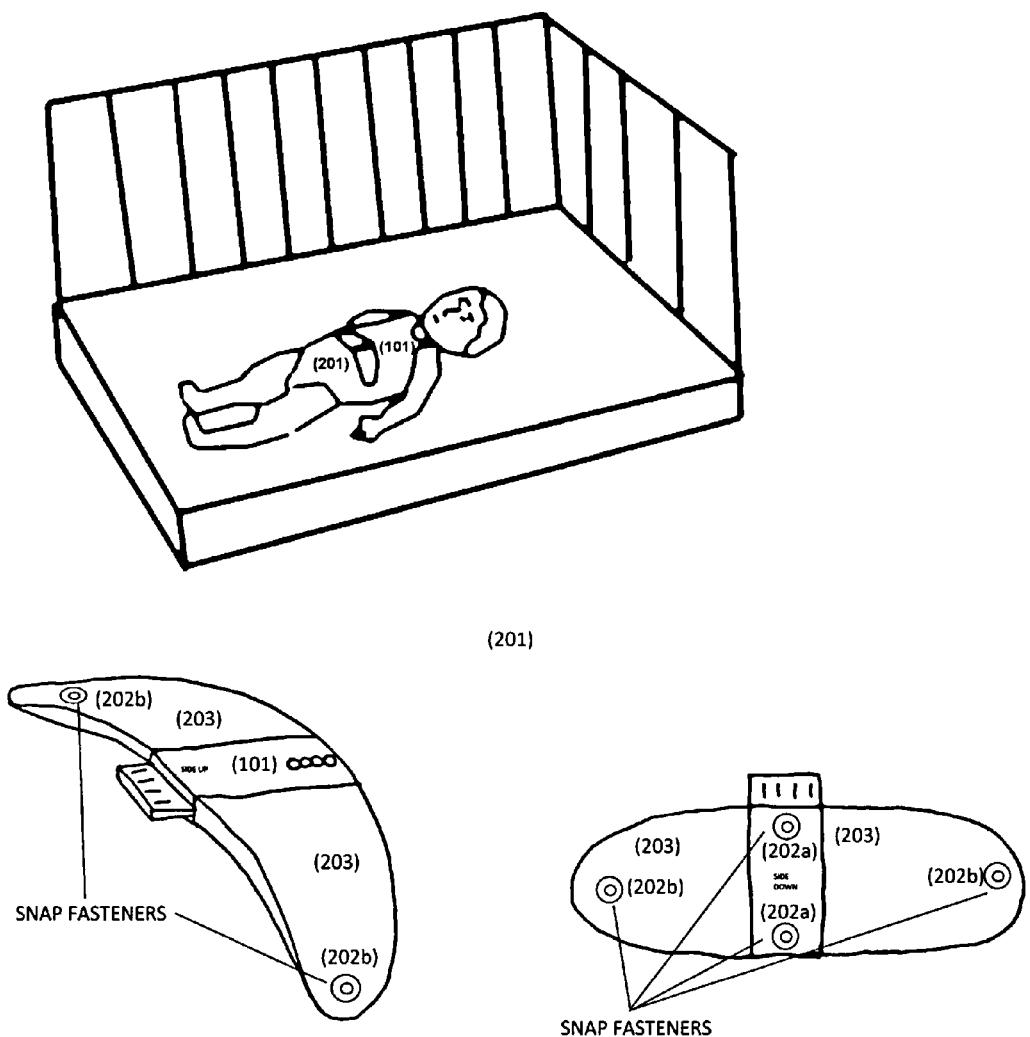
FIG. 2 illustrates the monitoring device positioned onto the stomach of the infant through the fixing system, while the infant is sleeping in its bed, and the preferred system used for attaching the device to the infant clothes.

Referring to FIG. 2, the monitoring device 101 is attached to the stomach of the infant through the securing system 201.

The securing system 201 is composed by a set of four snap fasteners 202; it should be clear to any person that the system can be attached to the leotard/clothes of the infant not only when it is sleeping, but also in other conditions (for instance, when it is in a car or in its pushchair). Two snap fasteners 202a are attached to the down side of the device housing, being the two corresponding fasteners parts inserted into the leotard, over the stomach; two additional snap fasteners 202b are attached at the extremities of two soft bands 203, strictly connected to the monitoring device 101, that are positioned over the stomach of the infant, being the two corresponding fasteners parts inserted into the leotard, on the two sides of the stomach. The overall shape of the monitoring device 101 and the fixing system is rounded, to maximize the comfort of the infant. The plastic enclosing the monitoring device 101 is also soft, to maximize the comfort of the infant. In an alternative embodiment, the two bands made of soft and elastic material could completely include the monitoring device 101, to further optimize the comfort of the infant.

The LED system 107 can be utilized to indicate to the caregivers that the monitoring device 101 is properly positioned on the infant body. This assumes that the caregiver controls the LEDs configuration when the infant is in supine position; the processing block 302 estimates the orientation of the monitoring device 101; for instance, when the Z axis of the tri-axial accelerometer 102 measures an acceleration close to 9.81 m/s2, then the block 302 activates the orange LED 107, otherwise the LED is off.

Figure 3:
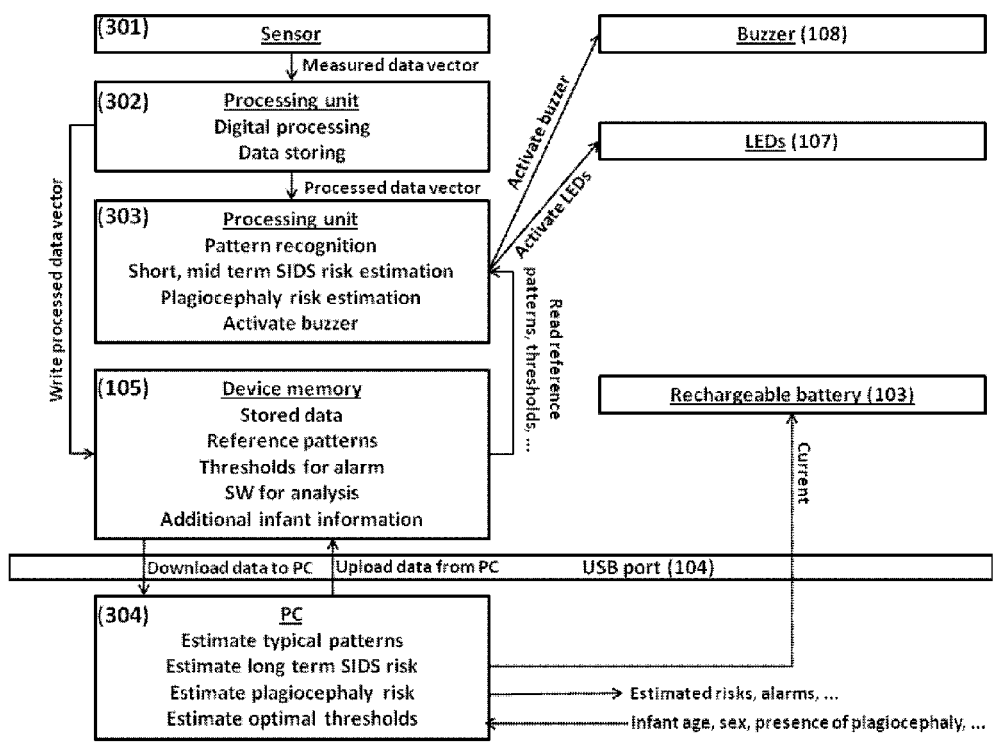
FIG. 3 shows a flow chart illustrating a method for estimating the low, mid and long term SIDS risk, the plagiocephaly risk and of optimizing the performance of the monitoring device.

Referring to FIG. 3, we distinguish a first group of methods aimed at estimating the short and mid term SIDS risks and the plagiocephaly risk, that are described in detail in the following.

Block 301 identifies the stage where the acceleration vector is measured by the accelerometer 102, converted in digital form and output as digital vector data.

Block 302 identifies the stage, in which the vector is acquired by the processing unit 106 and in which the processing unit 106 also digitally processes the vector to enhance the useful signal characteristics.

For instance, signal processing by the processing unit 106 could include, but is not limited to: a frequency band pass filter to enhance the presence of the frequency components typically associated to the breathing process; a large enough moving average filter to compute the mean acceleration vector measured in a certain amount of time, and therefore the orientation of the infant; the computation of the variance of the signal, which is associated, when beyond a predefined threshold, to the state of awakens of the infant. In general, any digital processing which highlights the desired characteristic of the signal, can be performed by the processing unit 106. The output of block 302 is a vector of features, which characterizes the properties of the measured signal. A typical vector of features could for instance be composed by a set of parameters such as the infant orientation, the signal variance, the dominant frequency, and so on. Moreover, the block 302 sends the processed data to the system memory 105 for saving them.

Block 303 identifies a further stage, in which the processing unit 106 compares the measured vector of features with the reference ones, that are stored into the device memory 105; then associates the measured data to one of the reference patterns, thus realizing a pattern recognition algorithm. A set of typical patterns could be used for describing, for instance, the following typical situations: infant not breathing, sleeping prone, sleeping supine, sleeping on side, awake, but other reference patterns could be included to obtain a more general functioning of the system, as, for instance, sleeping in a moving car, not breathing in a car, infant in a pushchair, and so on.

After pattern recognition has been performed, the processing unit 106 estimates the risks associated to the recognized pattern or, more generally, the risks associated with the sequence of measured pattern. For instance, recognizing a "infant not breathing" situation for as long as 2 seconds can be associated to a short apnea of the infant, where recognizing the same situation for as long as 10 seconds can be associated to a high short term SIDS risk—in the same manner, registering a "sleeping on right side" pattern for as long as 10 minutes does not constitute a high plagiocephaly risk situation, but the risk increases as the same situation is recorded for a longer period of time.

In the functioning mode dedicated to solo plagiocephaly risk assessment, the monitoring device 101 measures only the orientation of the head, not the breathing of the infant. Data are stored into the device memory 105 by block 302 and can also be transferred offline to a PC through the USB port 104.

When one of the risks is above a predefined threshold, which is stored in the device memory 105, the processing unit 106 activates the buzzer 108 which emits different kinds of alarm, depending on the kind of risk revealed.

In case of short term SIDS risk, the alarm could also be used to reactivate the infant breathing. In a similar manner, the processing unit 106 can activate the buzzer 108 when the infant lies on the right or left side for a long period of time, with the aim of forcing the infant to move and therefore limiting the risk of plagiocephaly.

Additional information can be included into the device memory 105 and used to activate the alarm signals in a optimal way; for instance, if the infant suffers a plagiocephaly on the right side of his head, the alarm signal could be emitted each time he turns on its right side, thus alerting the caregiver that the infant has to be turned, or even forcing the infant to turn by himself, because of the noise emitted by the buzzer 108. Another type of information that can be included in the device memory 105 is regarding sex and age of the infant, or other important information, as the SIDS risk can be different for male and female and can vary with the age.

For estimating the long term SIDS risk, the processing unit 106 stores each measured data vector into the device memory 105; stored data can then be downloaded to a PC through the USB port for further processing. Besides the measured data, also pattern data generated by the processing unit 106 can be downloaded and analyzed.

The device memory 105 also includes the software for data analysis, that can be downloaded to any PC together with the stored data. This fact increases the portability of the monitoring device 101, as any PC can be used for analyzing the recorded data. Furthermore, the historical data of the infant can also be included into the device memory 105, such that his entire history can always be downloaded and analyzed if necessary.

Block 304 identifies the stage where further processing is performed by a generic PC, based on the analysis software and the infant historical data downloaded (eventually in different times) from the memory 105 of the monitoring device 101.

First the analysis software executable code is downloaded on the PC and the analysis software program is automatically run.

If the amount of data is sufficiently large, the data analysis software estimates the typical behavior of the infant during the night; for instance, the percentage of time passed in prone, side or supine position, the number and the length of apneas and so on can be estimated.

Based on these data, a personalized risk of SIDS can be computed and communicated to the caregiver.

For instance, if the analysis software estimates that the infant passes the most part of his time sleeping prone, an alarm associated with a long term SIDS risk can be generated. An even more accurate estimate of this risk is obtained if the caregiver provides additional information to the analysis software, such as the age, the sex and the weight of the infant.

In a similar manner, analyzing the typical orientation of the infant during the sleeping period, the risk of onset of positional plagiocephaly is evaluated by the data analysis software and communicated to the caregiver. For instance, if the analysis software estimates that the infant passes the most part of his sleeping time on his right side, an alarm for possible onset of right positional plagiocephaly can be generated.

The information about the percentage of time passed on the right side (or left side, or prone, or supine) can be utilized by the caregivers to review the efficacy of the eventual repositioning strategy.

Also in this case, the additional information present in the device memory 105 can be utilized to optimize the risk evaluation.

For instance, if the infant exhibits a skull compression on the right side, such information can be registered in the device memory 105; the analysis software, in such case, can generate a positional plagiocephaly alarm when there is a slight predominance of time passed on the right side by the infant, while it does not generate any alarm when the infant passes the most of his time on the left side.

It has to be noted that the analysis software in block 304 does not only process the registered data and communicate the results (for instance, the estimated risks) to the caregivers, but also receives the additional information about the infant from the caregivers, such as for example sex and age, and stores them into the device memory 105.

In the present invention we further distinguish a group of methods aimed at optimizing the performance of the monitoring device 105, that are based on the supervised or unsupervised analysis of the recorded data, performed by the analysis software provided with the monitoring device 101 and run on the PC.

In case of unsupervised analysis, the registered data are automatically clustered into different classes, each associated to a different pattern; an average feature vector is then estimated for each class, and saved through the USB port 104 into the device memory 105 as new reference pattern. In this manner, the reference patterns used for identifying the different states of the infant are constantly updated and specifically tailored to the specific infant.

In case of supervised analysis, the caregiver provides information about the events occurred during the data registration period, for instance the occurrence of a false alarm or period of sleep of the infant. Based on these data, the thresholds and the reference patterns are updated by the analysis software and registered into the device memory 105 through the USB port 104.

Figure 4:
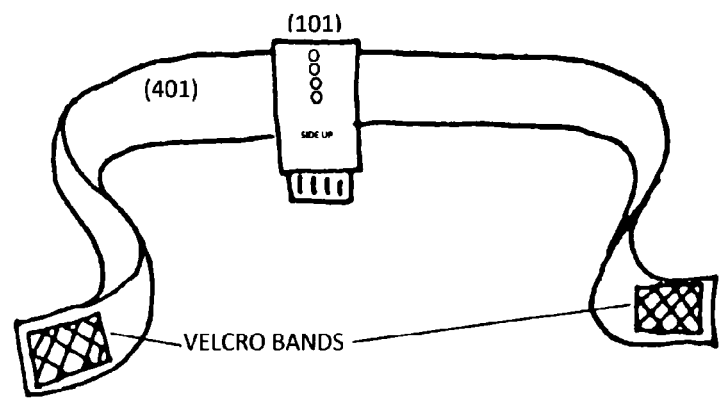
FIG. 4 illustrate two alternative systems used for fixing the monitoring device to the head of an infant, though a hook-and-loop fastener band or onto the baby's cap, for accurate measurement of the risk of positional plagiocephaly.
Figure 4:
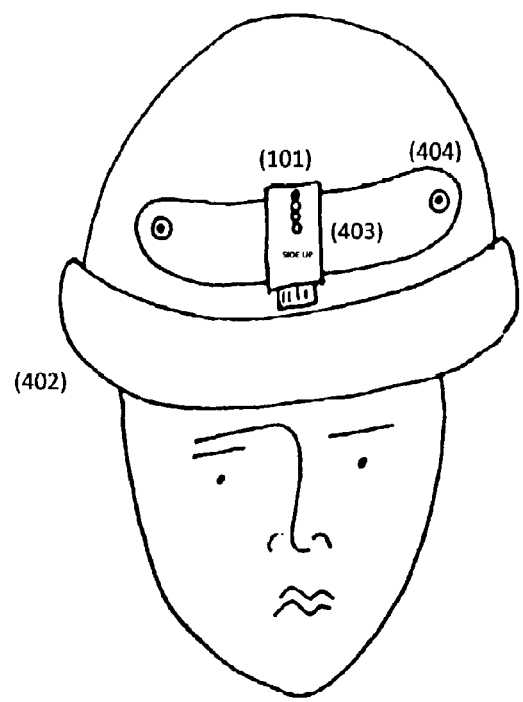

Referring to FIG. 4, alternative fixing systems are also described as a part of the invention.

These can be particularly useful when the risk of plagiocephaly has to be estimated with high accuracy.

It has to be noted that, although the risk of SIDS suddenly goes to zero when the infant is one year old, controlling the orientation of the infant during the sleeping time is significant for plagiocephaly up to an age of two years, when the skull becomes definitively rigid.

In this case, a hook-and-loop fastener band 401 (for instance a VELCRO band) is used to attach the device at the head 402 of the infant, such that the exact orientation of the head can be measured by the monitoring device 101.

Alternatively, a set of two bands 403 equipped with two snap fasteners 404 can be used to fix the monitoring device 101 to the baby's cap.

In the following various aspects of the system described herein are described in more detail oriented on various objects of the invention.

A first object is to provide a method and a monitoring device for measuring the short term, mid term and long term risk of SIDS for an infant, with high level of reliability and minimum instances of false risk detections.

For the purpose of achieving the first object of measuring the short term, mid term and long term SIDS risk, the monitoring device 101 is equipped with the a tri-axial accelerometer 102 and the control circuit or processing unit 106 which analyzes in real time the output tri-axial accelerometer 102; the processing unit 106 is therefore capable of measuring the moving activity, the breathing activity and the orientation of the infant. Based on processing of the measured data, the processing unit 106 can recognize at least five typical patterns, that are associated with different short term and mid term SIDS risk: infant awake, infant sleeping and breathing in a supine position, infant sleeping and breathing in a side position, infant sleeping and breathing in a prone position, infant not breathing. In practice, the monitoring device 101 is attached to the infant stomach and it is equipped with the a tri-axial accelerometer 102 which is capable of measuring the local acceleration vector; the processing unit 106 analyzes in real time a sequence of the data output from the accelerometer 102, and extracts characteristic features from the last train of signals (e.g. average value during the last 10 seconds, standard deviation during the last 10 seconds, dominant frequency) to recognize one of the five typical patterns cited above. The same processing unit 106 analyzes the zero frequency component of the measured signal to estimate the infant orientation.

The object of estimating the short term SIDS risk is achieved in real time by the processing unit 106 on board of the monitoring device 101, using a parametric statistical method for analyzing the output of the accelerometer 102. In particular, comparing in real time the typical acceleration pattern with the measured one, the processing unit 106 is capable of identifying the absence of breath in the infant, which corresponds to a high short term SIDS risk. Through a more general pattern analysis including a larger set of recognizable states, the processing unit 106 can differentiate between different states of the infant (awake (moving), sleeping and breathing in a supine position, sleeping and breathing in a side position, sleeping and breathing in a prone position, in the car, in the baby trolley, not breathing), each associated with different short term SIDS risks.

A method for achieving the object of estimating the mid term SIDS risk is also implemented in the processing unit 106. In particular, filtering out the high frequency components of the measured acceleration, the orientation of the monitoring device 101 with respect to the gravity force can be estimated. Under the hypothesis that the monitoring device 101 has been attached to the infant clothes in the proper manner (e.g. oriented such that the Z axis of the tri-axial accelerometer 102 is approximately parallel to the gravity force when the infant is supine), the orientation of the infant during the sleep is consequently estimated. Depending on the measured orientation (prone, side, supine), the corresponding mid term SIDS risk is estimated.

For the purpose of achieving the above described object of measuring the long term SIDS risk, the monitoring device 101 is equipped with a on board flash memory 105, such that the measured data can be stored in electronic format. Data registration is performed by the processing unit 106, that quantizes the three channels of the accelerometer output and records them into the device memory 105. Under the hypothesis that each channel of the accelerometer 102 requires 16 bit, and the sampling frequency is 30 Hz, it generates as much as 30 Hz*60 s*60 min*24 h*2 byte*3 channels=16 Mbyte/day of data. Hence, a memory 105 as large as 50 MB appears to be sufficient to record 2 days of data; the same memory 105 can contain, at the same time, the software for estimating the long term SIDS risk; this can be downloaded on a PC, together with the measured data, through the USB port 104 mounted onto the monitoring device 101. In this sense, the technology used for storing and downloading the data and the analysis software on the PC is similar to that of many MP3 music players. For estimating the long term SIDS risk, a method based on the statistical analysis of the typical sleep pattern is provided. The statistical analysis of the typical sleeping pattern (percentage of prone/side/supine sleep, average number of detected apneas, average number of movements occurring during the sleep, typical breath intensity and so on . . . ) permits to estimate the long term SIDS risk. As already mentioned, the software for performing the statistical analysis of the sleep pattern is stored into the same memory space where the data are recorded, ready for download and install each time the monitoring device 101 is attached to a PC.

The system of LEDs 107 mounted on board of the monitoring device 101 is used to signal different kinds of information to the user, for instance the green LED can indicate that the monitoring device 101 is working properly, whereas the red one could indicate that the battery 103 has to be recharged, and so on. The LEDs 107 can furthermore be used to indicate the correct positioning (or not) of the accelerometer 102 on the infant body.

A second object is to provide a method and a device for measuring the risk of onset of positional plagiocephaly and for measuring the efficacy of the eventual repositioning strategy actuated to oppose it. An alternative method is also provided for the very accurate measurement of the risk of plagiocephaly, together with a system and method for the positioning of the sensor device.

For the purpose of achieving the object of estimating the risk of onset of positional plagiocephaly, the infant orientation data recorded over a large enough amount of time are analyzed, with the aim of identifying (if present) the preferred sleeping position of the infant. A dominant sleeping position on the right or left side can then be associated to a high risk of onset of positional plagiocephaly. This objective is achieved together with that of measuring the SIDS risk, with the monitoring device 101 positioned onto the stomach of the infant. To get an even more accurate estimation of the risk of plagiocephaly, a hook- and loop fastener band, a soft helmet or similar fixing systems can be used to attach the monitoring device 101 to the head of the infant; in this case the proper orientation of the accelerometer 102 can be indicated by an adequate marking on the enclosure of the same monitoring device 101, and/or by the lightening of LED 107 indicators commanded by the acceleration signal measured in real-time.

When operating in this alternative mode, the monitoring device 101 is instructed not to recognize the infant breath, but only to measure the head orientation and store the data into the on board memory 105. Data are then downloaded onto a PC and processed by the software, to quantify the percentage of time associated to different head orientations. In case that a dominant head positioning mode is revealed, the caregiver is alerted with a visual or sound alarm emitted by the PC that a high risk of onset of positional plagiocephaly is present.

Alerting a caregiver, in presence of a potentially high SIDS risk and/or positional plagiocephaly, constitute a third object of the present system.

For the purpose of achieving the third object of alerting a caregiver in presence of a high short, mid or long term SIDS risk, different components and methods are provided in the present system. In particular, comparing in real time the typical acceleration pattern with the measured one, the processing unit 106 is capable of identifying the absence of breath in the infant; in this case (high short term risk), an acoustic signal is emitted by the buzzer 108 mounted on board of the monitoring device 101, in order to alert a caregiver and require his intervention. A different signal can be emitted when a prone or side sleeping position is detected for a certain amount of time (high mid term risk), in order to alert the caregiver. The monitoring device 101 can also be coupled with a microphone/receiver system, a wireless communication system or any other system which allows a signal to be transmitted at a certain distance; this allows the alarm to be heard by the caregiver also when he/she is distant from the infant (for instance in another room); however, it is to be noted that the transmission system is not necessary for the proper functioning of the monitoring device 101.

With the purpose of alerting the caregiver of a high long term SIDS risk, the data analysis SW is capable of alerting the caregiver (for instance by a window on the PC screen) that the long term risk is high and a specialist consult of the infant should be performed. Analyzing the typical orientation assumed by the infant during one or more nights, the same software can estimate the risk of onset of positional plagiocephaly and alert the caregiver when the risk is beyond a predefined threshold.

A fourth object is to provide a device and a method for stimulating the infant, with the aim of reactivating the breath process and/or forcing a change of position of the infant; this can be useful when a significant short or mid term SIDS risk is measured (that is, when the breath is absent, or in presence of a risky orientation of the infant during sleep), or when the permanence of the infant on the same side for a long time significantly increases the risk of plagiocephaly.

For the purpose of achieving the fourth object of reactivating the infant breath, or forcing him to change position, the buzzer 108 can be activated, using a different tone and volume with respect to the case of alarm, when the low term or mid term risk of SIDS are above a predefined threshold. In the same manner, when the infant lies on the same side for too long, the buzzer can be activated to force him changing his position, thus limiting the risk of developing plagiocephaly.

The monitoring device 101 could also be instructed to emit a sound each time the infant lies on the side affected by plagiocephaly, with the aim of making him lie on the other side and therefore forcing the correct sleeping position.

A fifth object is to provide a monitoring device characterized by ease of transportation and use outside of the home environment.

For achieving the fifth object of easy transportation and use of the system also outside of the home environment, the monitoring device 101 is constructed as a single, small piece, that can be easily attached to the clothes of the infant and work for a long period of time without the need of any supervision.

No power inlet is necessary to energize the monitoring device 101: to the scope, it is equipped with the rechargeable battery 103 and with the USB port 104. Thanks to the low power consumption, the monitoring device 101 can work as long as 24 hours or more without the need of recharging the battery 103. Anyway, even in case of low battery level, any standard USB port (nowadays available on any PC or even in most cars) can be used to recharge it. Therefore, once attached to the infant clothes, the monitoring device 101 continues to work even when the infant is moved out from his bed (e.g. walking with the pushchair or placed in a cradle). Moreover, nothing but the single-piece monitoring device 101 has to be taken out from home (under the hypothesis of availability of a USB port), even when the infant stays out of home for a long period of time (e.g. on holidays). A further device which could be used together with the invention, but it is not necessary for its proper functioning, is a base with one or more USB ports, connectable to the power net, which can be used for recharging the monitoring device 101 at home, without needing any available PC.

A method and means for properly and safely attaching the monitoring device 101 to the clothes of the infant, minimizing the possibility of ingestion and maximizing at the same time the comfort for the infant, and the corresponding fixing system, constitute a sixth object of the present invention.

For the purpose of achieving the above described object of having a correct and safe fixation to the infant clothes, as necessary for the reliable measuring of the infant orientation, the monitoring device 101 is provided with marking and fixing accessories facilitating its set up by the caregiver.

In a first embodiment the fixation system and method consist in placing the monitoring device 101 correctly oriented on the stomach of the infant, with the accelerometer 102 approximately oriented with one of the three axes parallel to the gravity force, when the infant is in a supine position. To this aim, one side of the monitoring device 101 is marked with a signal or with an inscription (e.g. "side up"), to suggest the proper orientation.

Furthermore, the colored LEDs 107 can be utilized to inform the caregivers about the correct sensor positioning (when, for instance, the infant is in a supine position and an average acceleration of approximately 1 g is registered along the Z axis).

In an alternative embodiment, the housing of the monitoring device 101 is built such that it can be positioned onto the infant clothes only in the proper orientation (e.g. a set of two snap fasteners is included on one side of the housing, and it permits to hook the monitoring device 101 to the clothes).

The system for attaching the monitoring device 101 to the infant clothes and the housing of the device are also optimized to limit the probability of ingestion. In particular, the housing of the monitoring device 101 can include a set of two bands that are large enough to avoid that the entire monitoring device 101 can enter into the mouth of the infant. Two snap fasteners, used to secure the monitoring device 101 to the clothes of the infant, are accommodated at the extremities of the bands. Other systems used to safely lock the monitoring device 101 to the clothes of the infant may include a short rope, an anterior pocket on the infant clothes, or other securing means. The housing material is preferably soft, to ensure the comfort of the infant, and water proof, to ensure protection of circuit from vomit or other liquids.

It is finally a seventh object to provide methods and means for optimizing the reliability in computing the short, mid and long term SIDS risk, by means of data storing, downloading on a PC and analyzing them through a supervised or unsupervised approach. In particular, in this manner the monitoring device 101 adapts to work properly in very different environmental situations or on very different infants. The recorded data can also be used for constructing the clinical case history of the infant.

For the purpose of achieving the above described object of optimizing the reliability of the monitoring device 101 (that is, for minimizing the possibility of false alarms, avoiding at the same time the probability of losing a potentially dangerous event, and to permit the reliable recognition of the dangerous states in different environmental conditions, or on infants with significantly different anatomic characteristics), the present invention provides at least two different methods for updating the parameters of the algorithms used by the processing unit for signal processing.

If the caregiver is capable to give a reliable feedback (for instance, he knows that a false alarm short term SIDS risk occurred at 10.02 PM of the last night), the parameters of the statistical model and/or the thresholds used for identifying the absence of breath can be consequently adjusted. In the same manner, the typical patterns associated to the breathing/not breathing conditions can be consequently updated.

A second manner for optimizing the functioning of the monitoring device 101 is represented by unsupervised learning: the software provided with the monitoring device 101 can analyze the registered data and divide them (clustering and/or learning mode) into different classes of pattern (e.g. sleeping period vs. active moving period), then it can estimate the typical acceleration patterns for each of them and use the average patterns as a reference for future statistical analysis (pattern recognition mode). Lastly, the thresholds adopted for emitting alarms through the buzzer 108 can be updated on the basis of the estimated long term SIDS or plagiocephaly risks; for instance, if an infant mainly sleeps on his right side, the alarm for plagiocephaly could be emitted after one hour of right side sleeping, but only after three hours of left side sleeping. In a similar manner, if an infant has a high long term SIDS risk, the alarm for a high short term SIDS risk can be emitted after a short period of not breathing time (apnea).

It should be noted that the monitoring device 101 can also be connectable to a wearable subunit which contains another accelerometer for collecting more data on the movement of the infant.

It should be noted that software to be executed on a PC can be a computer program product, that contains code for implementing the method described herein, if the code is executed by a processor in a computer. In some embodiments, the computer program product may be code stored on a computer readable data carrier such as a disc, a compact disc or a digital versatile disc or the like. In other embodiments, the computer program product may also be code stored on a data storage unit on a server or an array of servers. Such a data storage unit may be a hard disc or an array of hard disc or the like. In further embodiments, the data carrier may also be an electrical carrier signal that can be used for transferring the code from the web server or from any other server, which can be used for downloading the program code to a computer.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds or groups described in conjunction with a particular aspect, embodiment or example of the invention are to be understood to be applicable to any other aspect, embodiment or example described herein unless incompatible therewith.

REFERENCES

[1] U.S. Pat. No. 4,440,177
[2] U.S. Pat. No. 4,738,266
[3] US 2002133067
[4] U.S. Pat. No. 6,047,201
[5] US 2007244404
[6] US 2006047217
[7] US 2006020221
[8] JP 2008048819
[9] U.S. Pat. No. 5,505,199
[10] US 2006097879
[11] US 2010081895
[12] U.S. Pat. No. 5,515,865
[13] www.angelcare-monitor.com/
[14] U.S. Pat. No. 6,373,392
[15] U.S. Pat. No. 5,914,660
[16] U.S. Pat. No. 6,150,941
[17] WO 9618176
[18] U.S. Pat. No. 5,864,291
[19] CA 2207322
[20] U.S. Pat. No. 5,241,300
[21] WO 2008079296
[22] US 2008015457
[23] U.S. Pat. No. 6,765,489
[24] US 2008/0262381
[25] Turk A E, McCarthy J G, Thorne C H, Wisoff J H (1996). "The "back to sleep campaign" and deformational plagiocephaly: is there cause for concern?". J Craniofac Surg 7 (1): 12-8.
[26] Caccamese J, Costello B J, Ruiz R L, Ritter A M (2004). "Positional plagiocephaly: evaluation and management". Oral Maxillofac Surg Clin North Am 16 (4): 439-46.
[27] http://www.nichd.nih.gov/SIDS/upload/SIDS_rate_back_sleep_2006.pdf
[28] Use of corrective infant helmet, U.S. Pat. No. 7,153,284
[29] John Persing, Hector James, Jack Swanson, John Kattwinkel, Prevention and Management of Positional Skull Deformities in Infants, Pediatrics 2003; 112; 199-202, available at http://www.pediatrics.org/cgi/content/full/112/1/199.
[30] Method for correcting deformational plagiocephaly and other cranial deformations U.S. Pat. No. 7,698,763

The invention claimed is:

1. A method for performing the monitoring of the risks of Sudden Infant Death Syndrome (SIDS), and positional plagiocephaly, comprising the method steps of:
providing at least one sensor device capable of converting at least one physical magnitude into at least one electrical signal associated to the typical breath and positioning patterns of an infant;
providing a processing unit capable of acquiring from the sensor device the generated electrical signal, converting the electrical signal in numeric signal data and storing the signal data into a local memory;
using the processing unit for processing the stored signal data and for generating different kind of alarms for SIDS and plagiocephaly for the caregiver whenever a risk of SIDS or plagiocephaly above a predefined threshold is detected;
wherein
at least one of the sensor devices and the processing unit are disposed within a common housing forming a single wearable monitoring device, which is attached to the infant clothes or to the infant head; that
an energy storage of the monitoring device is provided with energy allowing continued operation without recharge for an autonomous operation period of at least 12 hours; that
numerical signal data generated during the operation period are transferred to the local memory during the operation period; that
the processing unit utilizes statistical analysis and/or pattern recognition algorithms, applied in real time to the signal data, for estimating a short and mid term risk for SIDS and plagiocephaly during the current operation period and for generating different kind of alarms for SIDS and plagiocephaly; and that
the data stored in the local memory are downloaded on an external processing unit and a statistical analysis, clustering and/or pattern recognition algorithm is applied to the data of more than one operation period to estimate a long term risk of SIDS or plagiocephaly, and/or to optimize the reliability of the monitoring device with respect to the particular environment and/or infant characteristics.

2. The method according to claim 1,
wherein the at least one sensor devices measure the infant movements and/or the infant body and/or head orientation by at least one tri-axial accelerometer.

3. The method according to claim 1,
wherein the monitoring device is safely and comfortably attached to the infant by a system based on snap fasteners, hook-and-loop fastener bands or other securing means to allow for accompanying the infant in any desired sleeping location.

4. The method according to claim 1,
wherein the monitoring device is recharged through a standard USB port, and the same USB port is used for downloading data from the monitoring device to an external processing unit or to communicate with the monitoring device.

5. The method according to claim 1,
wherein:
a. the signal data are digitally processed in real time by the processing unit to extract characteristic signal features;
b. the processing unit performs in real time statistical analysis and/or pattern recognition on the extracted features, to identify different orientations and acceleration patterns, each pattern being associated with different short term or mid term risk of SIDS or risk of plagiocephaly;
c. the identifiable patterns are at least associated with the status conditions: "infant not breathing", "infant sleeping in prone position", "infant sleeping on left side", "infant sleeping on right side", "infant sleeping in supine position", "infant awake";
d. the processing unit generates a high_short_term_SIDS_risk alarm at least when the "infant not breathing" pattern is detected for a predefined amount of time;

e. the processing unit generates the high_mid_term_SIDS_risk alarm at least when one of the "infant sleeping in prone position/on left side/on right side" pattern is detected for a predefined amount of time;
f. the processing unit generates the high_plagiocephaly_risk alarm at least when one of the "infant sleeping on left side/on right side" pattern is detected for a predefined amount of time.

6. The method according to claim 1,
wherein the historical signal data and/or extracted patterns are downloaded on a external processing unit and are processed by an expert system for an identification of a long term SIDS risk and plagiocephaly onset risk, personalized for the infant, and for an adjustment of the parameters of the statistical model and/or reference pattern and/or the risk thresholds either automatically or based on the feedback from the caregiver.

7. The method according to claim 1,
wherein:
a. the processing unit utilizes a buzzer mounted on board of the monitoring device to stimulate the infant breathing or movements through a sound emission, when a high short/mid term SIDS risk or plagiocephaly risk is detected;
b. the processing unit utilizes a buzzer mounted on board of the monitoring device to stimulate the infant movements through a different sound emission, when the infant lies on the side affected by plagiocephaly.

8. A monitoring device for performing the monitoring of the risks of Sudden Infant Death Syndrome (SIDS) and plagiocephaly, comprising:
at least one sensor device capable of converting at least one physical magnitude into at least one electrical signal associated to the typical breath and positioning patterns of an infant;
a processing unit capable of acquiring electrical signal generated by the sensor device, converting the electrical signals in numeric signal data and storing the signal data into a local memory, and processing the stored signal data and generating different kinds of alarm for SIDS and plagiocephaly for the caregiver whenever a risk of SIDS or plagiocephaly above a predefined threshold is detected;
wherein
at least one of the sensor devices and the processing unit are disposed in a common housing forming a single monitoring device, which can be attached to the infant clothes or to the infant head, that
the monitoring device is provided with an energy storage allowing continued operation without recharge for an operation period of at least 12 hours; that
the local memory has a capacity which is sufficient for storing the signal data generated during the operation period; that
the processing unit is arranged for utilizing statistical analysis and/or pattern recognition algorithms, applied in real time to the signal data, to for estimating a short and mid term risk for SIDS an plagiocephaly during the current operation period and for generating different kind of alarms for SIDS and plagiocephaly; and that
the monitoring device is provided with a communication port, through which data stored in the local memory can be downloaded to an external communication unit.

9. The monitoring device according to claim 8,
wherein the at least one sensor device comprises a tri-axial accelerometer which measures the infant movements and/or the infant body and/or head orientation.

10. The monitoring device according to claim 8,
wherein the monitoring device is provided with a snap fasteners, hook-and-loop fastener bands or other securing means for safely and comfortably attaching the monitoring device to the infant.

11. The monitoring device according to claim 8,
wherein the monitoring device is rechargeable through a standard USB port, and the same USB port can be used for downloading data from the monitoring device to a external processing unit or to communicate with the monitoring device.

12. The monitoring device according to claim 8,
wherein the housing of the monitoring device is made from a soft material which is also water-resistant, to avoid potential circuit damage in case of vomits or contact with other liquids, and wherein the housing comprises a shape and size that avoid unwanted ingestion.

13. The monitoring device according to claim 8,
wherein:
a. the processing unit digitally processes the signal data in real time to extract characteristic signal features;
b. the processing unit performs in real time statistical analysis and/or pattern recognition on the extracted features, to identify different orientations and acceleration patterns, each pattern being associated with different short term or mid term risk of SIDS or risk of plagiocephaly;
c. the identifiable patterns are at least associated with the status conditions: "infant not breathing", "infant sleeping in prone position", "infant sleeping on left side", "infant sleeping on right side", "infant sleeping in supine position", "infant awake";
d. the processing unit generates a high_short_term_SIDS_risk alarm at least when the "infant not breathing" pattern is detected for a predefined amount of time;
e. the processing unit generates the high_mid_term_SIDS_risk alarm at least when one of the "infant sleeping in prone position/on left side/on right side" pattern is detected for a predefined amount of time.
f. the processing unit generates the high_plagiocephaly_risk alarm at least when one of the "infant sleeping on left side/on right side" pattern is detected for a predefined amount of time.

14. The monitoring device according to claim 8, wherein:
a. the processing unit utilizes the buzzer mounted on board of the monitoring device to stimulate the infant breathing or movements through a sound emission, when a high short/mid term SIDS risk or plagiocephaly risk is detected;
b. the processing unit utilizes the buzzer mounted on board of the monitoring device to stimulate the infant movements through a different sound emission, when the infant lies on the side affected by plagiocephaly.

15. A software program product including a tangible non-transitory computer readable medium, on which is stored a program for processing signal data generated by a monitoring device for monitoring the risks of Sudden Infant Death Syndrome (SIDS) and plagiocephaly,
wherein the software program product contains code that, when executed by a processor and when using the data generated by the monitoring device during more than one operation period of the monitoring device, performs the steps of:
determining a long term SIDS risk and plagiocephaly onset risk personalized for the infant, and of adjusting the parameters of a statistical model and/or reference pattern and/or a risk thresholds either automatically or based on the feedback from the caregiver.

16. The method according to claim 1, wherein the at least one sensor devices is attached at the head of the infant for measuring the exact orientation of the head.

17. The method according to claim 16, wherein the processing unit quantifies the percentage of time associated to different head orientations as measured by the at least one sensor devices and generate an alarm if a dominant head positioning mode is revealed.

18. The monitoring device according to claim 8, wherein the at least one sensor devices is configured for measuring the exact orientation of the head, and wherein the processing unit is configured to quantify the percentage of time associated to different head orientations as measured by the at least one sensor devices and generate an alarm if a dominant head positioning mode is revealed.

19. The software program product according to claim 15, wherein the code is further configured to perform the steps of:
   quantifying the percentage of time associated to different head orientations when using the data generated by the monitoring device, and
   generating an alarm if a dominant head positioning mode is revealed.

* * * * *